(12) United States Patent
Narula et al.

(10) Patent No.: US 12,384,973 B2
(45) Date of Patent: Aug. 12, 2025

(54) ZEOLITIC CATALYTIC CONVERSION OF ALCOHOLS TO HYDROCARBONS

(71) Applicant: UT-Battelle, LLC, Oak Ridge, TN (US)

(72) Inventors: Chaitanya K. Narula, Knoxville, TN (US); Brian H. Davison, Knoxville, TN (US); Martin Keller, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 24 days.

(21) Appl. No.: 18/236,717

(22) Filed: Aug. 22, 2023

(65) Prior Publication Data

US 2024/0034937 A1 Feb. 1, 2024

Related U.S. Application Data

(63) Continuation of application No. 15/908,944, filed on Mar. 1, 2018, now Pat. No. 11,773,333, which is a
(Continued)

(51) Int. Cl.
*B01J 19/00* (2006.01)
*B01J 29/06* (2006.01)
(Continued)

(52) U.S. Cl.
CPC .............. *C10G 3/49* (2013.01); *B01J 29/061* (2013.01); *B01J 29/072* (2013.01); *B01J 29/076* (2013.01);
(Continued)

(58) Field of Classification Search
CPC .... C10G 3/45; C10G 3/49; C10G 2300/1011; C10G 2300/1014; C10G 2300/4006;
(Continued)

(56) References Cited

U.S. PATENT DOCUMENTS 3,702,886 A   11/1972 Argauer et al.
3,894,107 A   7/1975 Butter et al.
(Continued)

FOREIGN PATENT DOCUMENTS

CN   101454423 A   6/2009
EA     006785 B1   2/2005
(Continued)

OTHER PUBLICATIONS

Inaba et al. ("Production of olefins from ethanol by Fe-supported zeolite catalysts." Green Chem., 2007, 9, 638-646) (Year: 2007).*
(Continued)

*Primary Examiner* — In Suk C Bullock
*Assistant Examiner* — Jason Y Chong
(74) *Attorney, Agent, or Firm* — Scully, Scott, Murphy & Presser, P.C.

(57) ABSTRACT

A method for converting an alcohol to a hydrocarbon, the method comprising contacting said alcohol with a metal-loaded zeolite catalyst at a temperature of at least 100° C. and up to 550° C., wherein said alcohol can be produced by a fermentation process, said metal is a positively-charged metal ion, and said metal-loaded zeolite catalyst is catalytically active for converting said alcohol to said hydrocarbon.

13 Claims, 4 Drawing Sheets

Time (minutes)

Related U.S. Application Data continuation of application No. 15/357,039, filed on Nov. 21, 2016, now Pat. No. 9,938,467, which is a continuation of application No. 14/293,248, filed on Jun. 2, 2014, now Pat. No. 9,533,921, which is a continuation of application No. 14/123,363, filed as application No. PCT/US2012/042399 on Jun. 14, 2012, now abandoned.

(60) Provisional application No. 61/497,256, filed on Jun. 15, 2011.

(51) Int. Cl.

| | |
|---|---|
| *B01J 29/072* | (2006.01) |
| *B01J 29/076* | (2006.01) |
| *B01J 29/46* | (2006.01) |
| *B01J 29/48* | (2006.01) |
| *B01J 35/40* | (2024.01) |
| *B01J 35/56* | (2024.01) |
| *B01J 37/02* | (2006.01) |
| *C07C 1/22* | (2006.01) |
| *C10G 3/00* | (2006.01) |
| *C12P 7/06* | (2006.01) |
| *C12P 7/08* | (2006.01) |
| *C12P 7/10* | (2006.01) |
| *C12P 7/16* | (2006.01) |
| *B01J 29/14* | (2006.01) |
| *B01J 29/16* | (2006.01) |
| *B01J 29/68* | (2006.01) |
| *B01J 29/69* | (2006.01) |
| *B01J 29/76* | (2006.01) |
| *B01J 29/78* | (2006.01) |

(52) U.S. Cl.
CPC ............. *B01J 29/46* (2013.01); *B01J 29/48* (2013.01); *B01J 35/40* (2024.01); *B01J 35/56* (2024.01); *B01J 37/0246* (2013.01); *C07C 1/22* (2013.01); *C10G 3/45* (2013.01); *C12P 7/06* (2013.01); *C12P 7/08* (2013.01); *C12P 7/10* (2013.01); *C12P 7/16* (2013.01); *B01J 29/143* (2013.01); *B01J 29/146* (2013.01); *B01J 29/163* (2013.01); *B01J 29/166* (2013.01); *B01J 29/68* (2013.01); *B01J 29/69* (2013.01); *B01J 29/7615* (2013.01); *B01J 29/7661* (2013.01); *B01J 29/7669* (2013.01); *B01J 29/7692* (2013.01); *B01J 29/7815* (2013.01); *B01J 29/7861* (2013.01); *B01J 29/7869* (2013.01); *B01J 29/7892* (2013.01); *B01J 2229/183* (2013.01); *B01J 2229/186* (2013.01); *C10G 2300/1011* (2013.01); *C10G 2300/1014* (2013.01); *C10G 2300/4006* (2013.01); *C10G 2400/02* (2013.01); *C10G 2400/04* (2013.01); *C10G 2400/08* (2013.01); *Y02E 50/10* (2013.01); *Y02P 30/20* (2015.11)

(58) Field of Classification Search
CPC ............ C10G 2400/02; C10G 2400/04; C10G 2400/08; B01J 29/061; B01J 29/072; B01J 29/076; B01J 29/143; B01J 29/146; B01J 29/163; B01J 29/166; B01J 29/46; B01J 29/48; B01J 29/68; B01J 29/69; B01J 29/7615; B01J 29/7661; B01J 29/7669; B01J 29/7692; B01J 29/7815; B01J 29/7861; B01J 29/7869; B01J 29/7892; B01J 35/40; B01J 35/56; B01J 37/0246; B01J 2229/183; B01J 2229/186; C07C 1/22; C12P 7/06; C12P 7/08; C12P 7/10; C12P 7/16; Y02E 50/10; Y02P 30/20

See application file for complete search history.

(56) References Cited

U.S. PATENT DOCUMENTS

| | | |
|---|---|---|
| 3,899,544 A | 8/1975 | Chang et al. |
| 3,928,483 A | 12/1975 | Chang et al. |
| 3,931,349 A | 1/1976 | Kuo |
| 3,969,427 A | 7/1976 | Bell et al. |
| 3,998,898 A | 12/1976 | Chang et al. |
| 3,998,899 A | 12/1976 | Daviduk et al. |
| 4,025,571 A | 5/1977 | Lago |
| 4,035,430 A | 7/1977 | Dwyer et al. |
| 4,058,576 A | 11/1977 | Chang et al. |
| 4,071,573 A | 1/1978 | Owen et al. |
| 4,138,440 A | 2/1979 | Chang et al. |
| 4,148,835 A | 4/1979 | Chen et al. |
| 4,278,565 A | 7/1981 | Chen et al. |
| 4,289,606 A | 9/1981 | Gladrow et al. |
| 4,338,475 A | 7/1982 | Pennington et al. |
| 4,404,414 A | 9/1983 | Penick et al. |
| 4,423,274 A | 12/1983 | Daviduk et al. |
| 4,427,789 A | 1/1984 | Miale et al. |
| 4,499,327 A | 2/1985 | Kaiser et al. |
| 4,524,234 A | 6/1985 | Kaiser |
| 4,596,704 A | 6/1986 | Miale et al. |
| 4,608,355 A | 8/1986 | Chu |
| 4,621,164 A | 11/1986 | Chang et al. |
| 4,690,903 A | 9/1987 | Chen et al. |
| 4,727,214 A | 2/1988 | Uytterhoeven et al. |
| 4,788,042 A | 11/1988 | March et al. |
| 4,788,369 A | 11/1988 | Marsh et al. |
| 4,822,939 A | 4/1989 | Chu |
| 4,849,093 A | 7/1989 | Vauk et al. |
| 4,851,606 A | 7/1989 | Ragonese et al. |
| 4,861,937 A | 8/1989 | Baacke et al. |
| 5,041,690 A | 8/1991 | Harandi et al. |
| 5,045,287 A | 9/1991 | Harandi et al. |
| 5,177,279 A | 1/1993 | Harandi |
| 5,491,270 A | 2/1996 | Chin et al. |
| 5,773,676 A | 6/1998 | Drake et al. |
| 6,046,373 A | 4/2000 | Sun |
| 6,323,383 B1 | 11/2001 | Tsuchida et al. |
| 6,426,442 B1 | 7/2002 | Ichikawa et al. |
| 7,872,054 B2 | 1/2011 | Cortright et al. |
| 9,278,892 B2 | 3/2016 | Narula et al. |
| 9,434,658 B2 | 9/2016 | Narula et al. |
| 9,533,921 B2 | 1/2017 | Narula et al. |
| 9,938,467 B2 | 4/2018 | Narula et al. |
| 2003/0018231 A1 | 1/2003 | Xu et al. |
| 2003/0171630 A1 | 9/2003 | Winder et al. |
| 2007/0087934 A1 | 4/2007 | R.M. Martens et al. |
| 2008/0103345 A1 | 5/2008 | Levin et al. |
| 2008/0287720 A1 | 11/2008 | Clark |
| 2010/0018503 A1 | 7/2010 | Karim et al. |
| 2010/0268000 A1 | 10/2010 | Parekh et al. |
| 2010/0304455 A1 | 12/2010 | Inoue et al. |
| 2011/0061290 A1 | 3/2011 | Aulich et al. |
| 2011/0152513 A1 | 6/2011 | Yao et al. |
| 2013/0217935 A1 | 8/2013 | Adam et al. |
| 2014/0100404 A1 | 4/2014 | Narula et al. |
| 2014/0148630 A1 | 5/2014 | Adam et al. |
| 2014/0171691 A1 | 6/2014 | Kortan et al. |
| 2015/0011813 A1 | 1/2015 | Narula et al. |

FOREIGN PATENT DOCUMENTS

| | | |
|---|---|---|
| EA | 015812 B1 | 12/2008 |
| EP | 0099650 | 2/1984 |
| EP | 0130368 | 1/1985 |
| RU | 2 082 500 C1 | 6/1997 |
| RU | 2163624 C | 2/2001 |
| RU | 2 407 778 C2 | 1/2010 |
| WO | WO 90/12855 A1 | 11/1990 |
| WO | WO 2007/020068 A1 | 2/2007 |

(56) References Cited

FOREIGN PATENT DOCUMENTS

| WO | WO 2007/112314 A2 | 10/2007 |
| WO | WO 2008/069841 A2 | 6/2008 |
| WO | WO 2008/069984 A2 | 6/2008 |
| WO | WO 2012/016787 A1 | 2/2012 |
| WO | WO 2012/174205 A1 | 12/2012 |
| WO | WO 2013/014081 A1 | 1/2013 |

OTHER PUBLICATIONS

Inaba et al. (Ethanol Conversion to Aromatic Hydrocarbons over Several Zeolite Catalysts. React. Kinet. Catal. Lett. vol. 88, No. 1, 135-142 (2006)) (Year: 2006).*
U.S. Final Office Action dated Aug. 29, 2017 issued in U.S. Appl. No. 14/878,663.
European Office Action dated Jun. 27, 2016 issued in corresponding European Patent Application No. 12 799 829.2.
Office Action dated Dec. 15, 2015 received in related U.S. Patent Application, namely U.S. Appl. No. 13/787,112.
U.S. Office Action issued in U.S. Appl. No. 14/263,257 on Aug. 19, 2015.
Chinese Office Action dated Jul. 9, 2015 received from Application No. 201280036737.8, together with an English-language translation.
U.S. Final Office Action dated Apr. 20, 2015 in U.S. Appl. No. 14/321,012.
U.S. Office Action dated Jan. 13, 2015 in U.S. Appl. No. 14/263,257.
Jurgen Schulz and Friedhelm Bandermann, Conversion of Ethanol over Metal-exchnaged Zeolites, Chem. Eng. Technol. 16, 1993, p. 332-337.
English-language translation of the Office Action dated Nov. 15, 2014 received from the Chinese Patent Office in Application No. 201280036737.8.
U.S. Office Action dated Dec. 2, 2014 in U.S. Appl. No. 14/321,012.
Supplementary Extended European Search Report dated Nov. 24, 2014 received from EP Application No. 12799829.2.
International Search Report and Written Opinion dated Oct. 30, 2014 received from International Application No. PCT/US2014/044999.
U.S. Office Action dated Oct. 21, 2014 in related U.S. Appl. No. 14/123,363.
International Search Report dated Sep. 27, 2012 received from related Application No. PCT/US2012/042399.
Written Opinion dated Sep. 27, 2012 received from the International Searching Authority in related Application No. PCT/US2012/042399.
Li, Z., et al., "Selective conversion of bio-derived ethanol to renewable BTX over Ga—ZSM-5", Green Chem., 2017, Accepted May 19, 2017, Published on Jun. 1, 2017, pp. 4344-4352, 1.
C.D. Chang et al., "Process Studies on the Conversion of Methanol to Gasoline" Ind. Eng. Chem. Process Des. Dev., 17(3), 255-260 (Jan. 9, 1978).
C.D. Chang et al.,"The Conversion of Methanol and Other O-Compounds to Hydrocarbons over Zeolite Catalysts", Journal of Catalysis, 47, 249-259, (Jan. 24, 1977).
U.S. Office Action dated Jun. 11, 2018 in U.S. Appl. No. 15/908,944.
U.S. Office Action dated Sep. 16, 2019 in U.S. Appl. No. 15/908,944.
U.S. Office Action dated Jul. 27, 2022 in U.S. Appl. No. 15/908,944.
U.S. Final Office Action dated Jan. 7, 2019 in U.S. Appl. No. 15/908,944.
U.S. Final Office Action dated Mar. 11, 2020 in U.S. Appl. No. 15/908,944.
U.S. Final Office Action dated Jun. 25, 2021 in U.S. Appl. No. 15/908,944.
U.S. Final Office Action dated Jan. 28, 2022 in U.S. Appl. No. 15/908,944.
U.S. Final Office Action dated Jan. 24, 2023 in U.S. Appl. No. 15/908,944.

* cited by examiner (4A)

(4B)

ZEOLITIC CATALYTIC CONVERSION OF ALCOHOLS TO HYDROCARBONS

CROSS REFERENCE TO RELATED APPLICATIONS

This application is a continuation of U.S. patent application Ser. No. 15/908,944 filed Mar. 1, 2018, which is a continuation of U.S. patent application Ser. No. 15/357,039 filed Nov. 21, 2016, which is a continuation of U.S. patent application Ser. No. 14/293,248 filed Jun. 2, 2014, which is a continuation of copending application Ser. No. 14/123,363 filed Dec. 10, 2013 which is a National Phase of PCT/US2012/042399 filed Jun. 14, 2012 which claims the benefit of priority from U.S. Provisional Application 61/497,256, filed on Jun. 15, 2011, all of the contents of which are incorporated herein by reference.

GOVERNMENT SUPPORT

This invention was made with government support under Prime Contract No. DE-AC05-00OR22725 awarded by the U.S. Department of Energy. The government has certain rights in the invention.

FIELD OF THE INVENTION

The present invention relates, generally, to the catalytic conversion of alcohols to hydrocarbons, and more particularly, to zeolite-based catalytic methods for such conversion.

BACKGROUND OF THE INVENTION

The conversion of alcohols to hydrocarbons is generally not commercially feasible. In fact, the majority of commercial alcohols are produced from hydrocarbons. Alcohol-to-hydrocarbon conversion is further prohibitive due to the significant cost requirements of current conversion processes. Hence, alcohol obtained by natural means (e.g., by fermentation of biomass) would be a significantly more cost-efficient feedstock.

However, a major obstacle in applying current conversion methodology to biomass-produced alcohols (i.e., bio-alcohols) is the high concentration of water (and concomitant low alcohol concentrations) typically encountered in fermentation streams produced in biomass-to-alcohol refineries. Current alcohol-to-hydrocarbon conversion processes are generally incapable or highly ineffective in providing such conversion at such dilute alcohol and high water concentrations. Instead, current alcohol-to-hydrocarbon conversion processes generally require pure alcohol (i.e., in the substantial absence of water). Moreover, concentration and/or distillation of alcohol from a fermentation stream to accommodate current technologies would be highly energy intensive, and thus, would largely offset gains made in the initial low cost of using a bio-alcohol.

SUMMARY OF THE INVENTION

The invention is directed to a method for catalytically converting an alcohol to a hydrocarbon, wherein the catalytic conversion is accomplished without requiring the alcohol to be purified or concentrated before the conversion reaction. For example, by methods described herein, effective conversion can be accomplished on dilute aqueous solutions of an alcohol, as found, for example, in the fermentation stream of a biomass fermentation reactor. In particular embodiments, the method includes contacting an alcohol (or mixture of alcohols) with a metal-loaded zeolite catalyst at a temperature of at least 100° C. and up to 550° C., wherein the alcohol can be (i.e., is capable of being, or is) produced by a fermentation process, the metal is a positively-charged metal ion, and the metal-loaded zeolite catalyst is catalytically active for converting the alcohol or mixture thereof to a hydrocarbon or mixture of hydrocarbons.

BRIEF DESCRIPTION OF THE DRAWINGS

(FIG. 3B) for V—ZSM-5 catalyst.

DETAILED DESCRIPTION OF THE INVENTION

Figure 1:
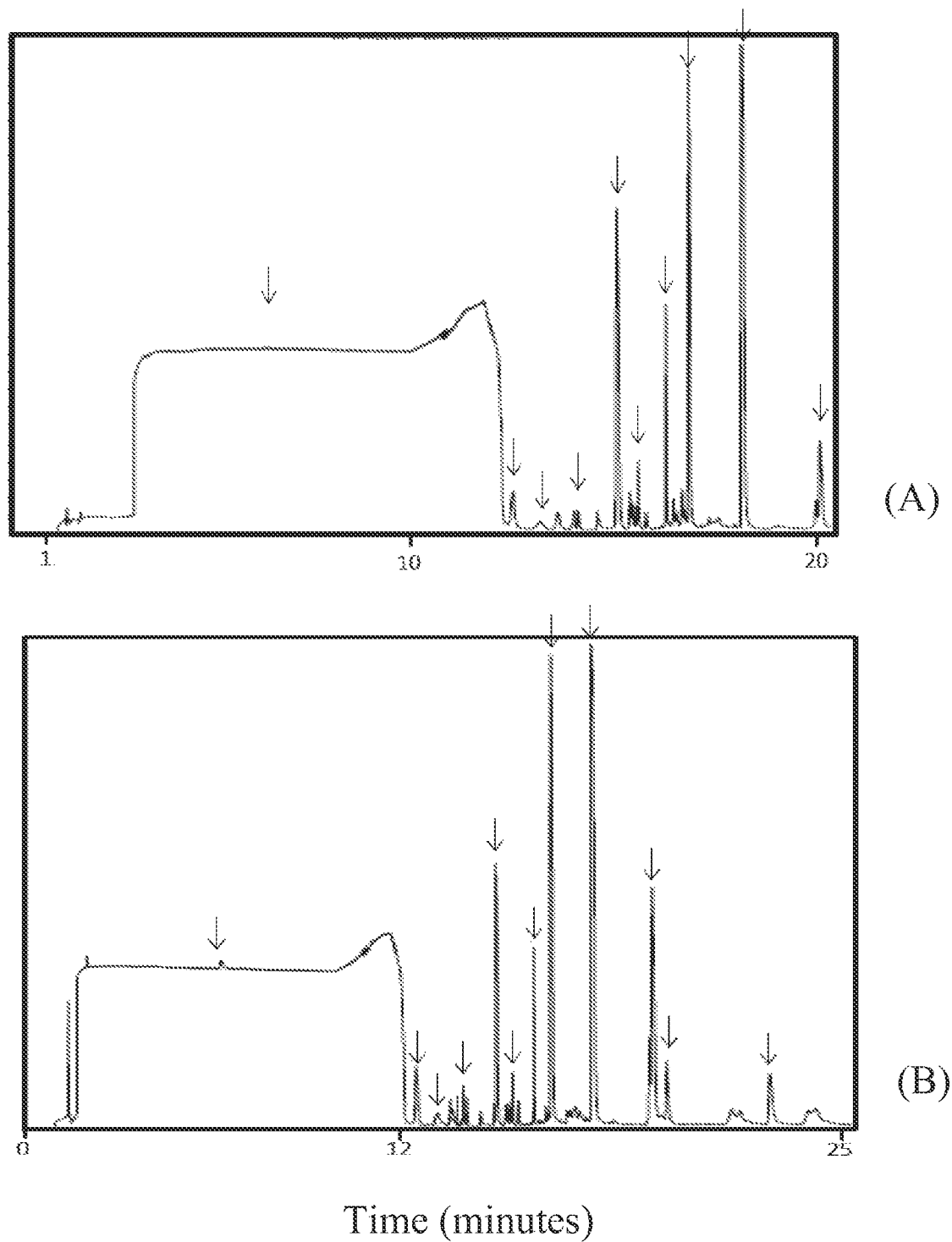
FIG. 1. Graph comparing hydrocarbon distribution between pure ethanol (A) and 10% ethanol in water (B) after catalytic conversion over Cu—ZSM-5 at 400° C. The compounds are (from left to right, identified by arrows) water, acetaldehyde, isobutene, 2-butene, acetone, 1,2-dimethyl-4-ethynyl-benzene, 2-butanone, benzene, toluene, 1,3-dimethylbenzyne, p-xylene, naphthalene, and phenol.

In the conversion method described herein, an alcohol is catalytically converted to a hydrocarbon by contacting the alcohol with a metal-loaded zeolite catalyst at conditions (particularly, temperature and choice of catalyst) suitable to effect said conversion. As used herein, the term "alcohol" is meant to include a single alcohol or a mixture of two or more alcohols, and the term "hydrocarbon" is likewise meant to include a single hydrocarbon compound or a mixture of two or more hydrocarbon compounds.

The alcohol considered herein is primarily one that can be produced by a fermentation process (i.e., a bio-alcohol). Most notable examples of bio-alcohols considered herein include ethanol, butanol, and isobutanol. In different embodiments, the alcohol can be ethanol, or butanol, or isobutanol, or a combination thereof, as commonly found in fermentation streams. In particular embodiments, the alcohol is an aqueous solution of alcohol (i.e., the alcohol is a component of an aqueous solution), as found in fermentation streams. In fermentation streams, the alcohol is typically in a concentration of no more than about 20% (vol/vol), 15%, 10%, or 5%. In some embodiments, a fermentation stream is directly contacted with the catalyst (typically, after filtration to remove solids) to effect the conversion of the alcohol in the fermentation stream. In other embodiments, the fermentation stream is concentrated in alcohol (for example, of at least or up to 30%, 40%, or 50%) before contacting the fermentation stream with the catalyst. In yet other embodiments, alcohol in the fermentation stream is selectively removed from the fermentation stream, such as by distillation, to produce a substantially pure form of alcohol as the feedstock (e.g., a concentration of at least 90% or 95% of alcohol). In still other embodiments, the alcohol is completely dewatered into 100% alcohol before contacting with the catalyst.

As used herein, the term "about" generally indicates within ±0.5%, 1%, 2%, 5%, or up to ±10% of the indicated value. For example, a concentration of about 20% generally indicates in its broadest sense 20±2%, which indicates 18-22%. In addition, the term "about" can indicate either a measurement error (i.e., by limitations in the measurement method), or alternatively, a variation or average in a physical characteristic of a group.

Although a wide variety of hydrocarbon product can be produced by the instant method, the hydrocarbon primarily considered herein is typically saturated, and more particularly, in the class of alkanes, which may be straight-chained, or branched, or a mixture thereof, particularly when the hydrocarbon product is to be used as a fuel. The alkanes particularly desired herein include those containing at least four, five, or six carbon atoms, and up to twelve, fourteen, sixteen, seventeen, eighteen, or twenty carbon atoms. Some examples of straight-chained alkanes include n-butane, n-pentane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, and n-eicosane. Some examples of branched alkanes include isobutane, isopentane, neopentane, isohexane, 3-methylpentane, 2,3-dimethylbutane, 2,2-dimethylbutane, 2-methylhexane, 3-methylhexane, 2,2-dimethylpentane, 2,3-dimethylpentane, 2,4-dimethylpentane, 3,3-dimethylpentane, 2-methylheptane, and 2,2,4-trimethylpentane (isooctane). Some other hydrocarbon products that may be produced by the instant method include olefins (i.e., alkenes, such as, for example, ethylene, propylene, n-butene, and/or isobutene) and aromatics (for example, naphthalene, benzene, toluene, and/or xylenes).

The hydrocarbon product particularly considered herein is a mixture of hydrocarbon compounds useful as a fuel or as a blendstock in fuel. The mixture of hydrocarbon compounds produced herein preferably substantially corresponds (e.g., in composition and/or properties) to a known petrochemical fuel, such as petroleum, or a fractional distillate of petroleum. Some examples of petrochemical fuels include gasoline, kerosene, diesel, and jet propellant (e.g., JP-8). Like hydrocarbon fuel grades in current use, the mixture of hydrocarbon compounds produced herein can, in some embodiments, be predominantly or exclusively composed of alkanes, alkenes, aromatics, or a mixture thereof. Although aromatics (particularly benzene) may be present in the hydrocarbon mixture, their presence may be minimized to adhere to current fuel standards. The raw hydrocarbon product, produced by the instantly described method, is typically fractionated by distillation into different fuel grades, each of which is known to be within a certain boiling point range. A particular advantage of the instant method is its ability to produce such fuel grades in the substantial absence of contaminants (e.g., mercaptans) normally required to be removed during the petroleum refining process. Moreover, by appropriate adjustment of the catalyst and processing conditions, a select distribution of hydrocarbons can be obtained.

Depending on the final composition of the hydrocarbon product, the product can be directed to a variety of applications, including, for example, as precursors for plastics, polymers, and fine chemicals. The process described herein can advantageously produce a range of hydrocarbon products that differ in any of a variety of characteristics, such as molecular weight (i.e., hydrocarbon weight distribution), degree of saturation or unsaturation (e.g., alkane to alkene ratio), and level of branched or cyclic isomers. The process provides this level of versatility by appropriate selection of, for example, composition of the catalyst (e.g., catalytic metal), amount of catalyst (e.g., ratio of catalyst to alcohol precursor), processing temperature, and flow rate (e.g., LHSV).

In the process, a suitable reaction temperature is employed during contact of the alcohol with the catalyst. Generally, the reaction temperature is at least 100° C. and up to 550° C. In different embodiments, the reaction is precisely or about, for example, 100° C., 125° C., 150° C., 175° C., 200° C., 225° C., 250° C., 275° C., 300° C., 325° C., 350° C., 375° C., 400° C., 425° C., 450° C., 475° C., 500° C., 525° C., or 550° C., or a temperature within a range bounded by any two of the foregoing exemplary temperatures (e.g., 100° C.-550° C., 200° C.-550° C., 300° C.-550° C., 400° C.-550° C., 450° C.-550° C., 100° C.-500° C., 200° C.-500° C., 300° C.-500° C., 350° C.-500° C., 400° C.-500° C., 450° C.-500° C., 100° C.-450° C., 200° C.-450° C., 300° C.-450° C., 350° C.-450° C., 400° C.-450° C., 100° C.-425° C., 200° C.-425° C., 300° C.-425° C., 350° C.-425° C., 375° C.-425° C., 400° C.-425° C., 100° C.-400° C., 200° C.-400° C., 300° C.-400° C., 350° C.-400° C., and 375° C.-400° C.).

Generally, ambient (i.e., normal atmospheric) pressure of about 1 atm is used in the method described herein. However, in some embodiments, an elevated pressure or reduced pressure may be used. For example, in some embodiments, the pressure may be elevated to, for example, 1.5, 2, 3, 4, or 5 atm, or reduced to, for example, 0.5, 0.2, or 0.1 atm.

The catalyst and reactor can have any of the designs known in the art for catalytically treating a fluid or gas at elevated temperatures, such as a fluidized bed reactor. The process may be in a continuous or batch mode. In particular embodiments, the alcohol is injected into a heated reactor such that the alcohol is quickly volatilized into gas, and the gas passed over the catalyst. In some embodiments, the reactor design includes a boiler unit and a reactor unit if the fermentation stream is used directly as a feedstock without purification. The boiler unit is generally not needed if the fermentation stream is distilled to concentrate ethanol because the distillation process removes the dissolved solids in the fermentation streams. The boiler unit volatilizes liquid feedstock into gases prior to entry into the reactor unit and withholds dissolved solids.

In some embodiments, the conversion method described above is integrated with a fermentation process, wherein the fermentation process produces the alcohol used as feedstock for the conversion process. By being "integrated" is meant that alcohol produced at a fermentation facility or zone is sent to and processed at a conversion facility or zone (which performs the conversion process described above). Preferably, in order to minimize production costs, the fermentation process is in close enough proximity to the conversion facility or zone, or includes appropriate conduits for transferring produced alcohol to the conversion facility or zone, thereby not requiring the alcohol to be shipped. In particular embodiments, the fermentation stream produced in the fermentation facility is directly transferred to the conversion facility, generally with removal of solids from the raw stream (generally by filtration or settling) before contact of the stream with the catalyst.

In some embodiments, the fermentation process is performed in an autonomous fermentation facility, i.e., where saccharides, produced elsewhere, are loaded into the fermentation facility to produce alcohol. In other embodiments, the fermentation process is part of a larger biomass reactor facility, i.e., where biomass is decomposed into fermentable saccharides, which are then processed in a fermentation zone. Biomass reactors and fermentation facilities are well known in the art. Biomass often refers to lignocellulosic matter (i.e., plant material), such as wood, grass, leaves, paper, corn husks, sugar cane, bagasse, and nut hulls. Generally, biomass-to-ethanol conversion is performed by 1) pretreating biomass under well-known conditions to loosen lignin and hemicellulosic material from cellulosic material, 2) breaking down cellulosic material into fermentable saccharide material by the action of a cellulase enzyme, and 3) fermentation of the saccharide material, typically by the action of a fermenting organism, such as suitable yeast.

In other embodiments, the alcohol is produced from a more direct sugar source, such as a plant-based source of sugars, such as sugar cane or a grain starch (such as corn starch). Ethanol production via corn starch (i.e., corn starch ethanol) and via sugar cane (i.e., cane sugar ethanol) currently represent some of the largest commercial production methods of ethanol. Integration of the instant conversion process with any of these large scale ethanol production methods is contemplated herein.

The conversion catalyst used herein includes a zeolite portion and a metal loaded into the zeolite. The zeolite considered herein can be any of the porous aluminosilicate structures known in the art that are stable under high temperature conditions, i.e., of at least 100° C., 150° C., 200° C., 250° C., 300° C., and higher temperatures up to, for example, 500° C., 550° C., 600° C., 650° C., 700° C., 750° C., 800° C., 850° C., or 900° C. In particular embodiments, the zeolite is stable from at least 100° C. and up to 700° C. Typically, the zeolite is ordered by having a crystalline or partly crystalline structure. The zeolite can generally be described as a three-dimensional framework containing silicate ($SiO_2$ or $SiO_4$) and aluminate ($Al_2O_3$ or $AlO4$) units that are interconnected (i.e., crosslinked) by the sharing of oxygen atoms.

The zeolite can be microporous (i.e., pore size of less than 2 μm), mesoporous (i.e., pore size within 2-50 μm, or sub-range therein), or a combination thereof. In several embodiments, the zeolite material is completely or substantially microporous. By being completely or substantially microporous, the pore volume due to micropores can be, for example, 100%, or at least 95%, 96%, 97%, 98%, 99%, or 99.5%, with the remaining pore volume being due to mesopores, or in some embodiments, macropores (pore size greater than 50 μm). In other embodiments, the zeolite material is completely or substantially mesoporous. By being completely or substantially mesoporous, the pore volume due to mesopores can be, for example, 100%, or at least 95%, 96%, 97%, 98%, 99%, or 99.5%, with the remaining pore volume being due to micropores, or in some embodiments, macropores. In yet other embodiments, the zeolite material contains an abundance of both micropores and mesopores. By containing an abundance of both micropores and mesopores, the pore volume due to mesopores can be, for example, up to, at least, or precisely 50%, 60%, 70%, 80%, or 90%, with the pore volume balance being due to micropores, or vice-versa.

In various embodiments, the zeolite is a MFI-type zeolite, MEL-type zeolite, MTW-type zeolite, MCM-type zeolite, BEA-type zeolite, kaolin, or a faujasite-type of zeolite. Some particular examples of zeolites include the ZSM class of zeolites (e.g., ZSM-5, ZSM-8, ZSM-11, ZSM-12, ZSM-15, ZSM-23, ZSM-35, ZSM-38, ZSM-48), zeolite X, zeolite Y, zeolite beta, and the MCM class of zeolites (e.g., MCM-22 and MCM-49). The compositions, structures, and properties of these zeolites are well-known in the art, and have been described in detail, as found in, for example, U.S. Pat. Nos. 4,721,609, 4,596,704, 3,702,886, 7,459,413, and 4,427,789, the contents of which are incorporated herein by reference in their entirety.

The zeolite can have any suitable silica-to-alumina (i.e., $SiO_2/Al_2O_3$ or "Si/Al") ratio. For example, in various embodiments, the zeolite can have a Si/Al ratio of precisely, at least, less than, or up to 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 120, 150, or 200, or a Si/Al ratio within a range bounded by any two of the foregoing values. In particular embodiments, the zeolite possesses a Si/Al ratio of 1 to 45.

In particular embodiments, the zeolite is ZSM-5. ZSM-5 belongs to the pentasil-containing class of zeolites, all of which are also considered herein. In particular embodiments, the ZSM-5 zeolite is represented by the formula $Na_nAl_nSi_{96-n}O_{192} \cdot 16H_2O$, wherein $0<n<27$.

Typically, the zeolite contains an amount of cationic species. As is well known in the art, the amount of cationic species is generally proportional to the amount of aluminum in the zeolite. This is because the replacement of silicon atoms with lower valent aluminum atoms necessitates the presence of countercations to establish a charge balance. Some examples of cationic species include hydrogen ions ($H^+$), alkali metal ions, alkaline earth metal ions, and main group metal ions. Some examples of alkali metal ions that may be included in the zeolite include lithium ($Li^+$), sodium ($Na^+$), potassium ($K^+$), rubidium ($Rb^+$), and cesium ($Cs^+$). Some examples of alkaline earth metal ions that may be included in the zeolite include ($Be^{2+}$), magnesium ($Mg^{2+}$), calcium ($Ca^{2+}$), strontium ($Sr^{2+}$), and barium ($Ba^{2+}$). Some examples of main group metal ions that may be included in the zeolite include boron ($B^{3+}$), gallium ($Ga^{3+}$), indium ($In^{3+}$), and arsenic ($As^{3+}$). In some embodiments, a combination of cationic species is included. The cationic species can be in a trace amount (e.g., no more than 0.01 or 0.001%), or alternatively, in a significant amount (e.g., above 0.01%, and up to, for example, 0.1, 0.5, 1, 2, 3, 4, or 5% by weight of the zeolite). In some embodiments, any one or more of the above classes or specific examples of cationic species are excluded from the zeolite.

The zeolite described above is loaded with an amount of metal. The metal loaded into the zeolite is selected such that the resulting metal-loaded zeolite is catalytically active, under conditions set forth above, for converting an alcohol to a hydrocarbon. Typically, the metal considered herein is in the form of positively-charged metal ions (i.e., metal cations). The metal cations can be, for example, monovalent, divalent, trivalent, tetravalent, pentavalent, or hexavalent. In some embodiments, the metal is (or includes) alkali metal ions. In other embodiments, the metal is (or includes) alkaline earth metal ions. In other embodiments, the metal is (or includes) a transition metal, such as one or more first, second, or third row transition metals. Some preferred transition metals include copper, iron, zinc, titanium, vanadium, and cadmium. The copper ions can be cuprous ($Cu^{+1}$) or cupric ($Cu^{+2}$) in nature, and the iron atoms can be ferrous ($Fe^{+2}$) or ferric ($Fe^{+3}$) in nature. Vanadium ions may be in any of its known oxidation states, e.g., $V^{+2}$, $V^{+3}$, $V^{+4}$, and $V^{+5}$. In other embodiments, the metal is (or includes) a catalytically active main group metal, such as gallium or indium. A single metal or a combination of metals may be loaded into the zeolite. In other embodiments, any one or more metals described above are excluded from the zeolite.

The metal loading can be any suitable amount, but is generally no more than about 2.5%, wherein the loading is expressed as the amount of metal by weight of the zeolite. In different embodiments, the metal loading is precisely, at least, less than, or up to, for example, 0.01%, 0.02%, 0.03%, 0.04%, 0.05%, 0.06%, 0.07%, 0.08%, 0.09%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5%, or a metal loading within a range bounded by any two of the foregoing values.

In further aspects of the invention, the zeolite catalyst may include at least one trivalent metal ion in addition to one or more metals described above. As used herein, the term "trivalent metal ion" is defined as a trivalent metal ion other than aluminum ($Al^{+3}$). Without wishing to be bound by any theory, it is believed that the trivalent metal is incorporated into the zeolite structure. More specifically, the incorporated trivalent metal ion is believed to be bound in the zeolite to an appropriate number of oxygen atoms, i.e., as a metal oxide unit containing the metal cation connected to the structure via oxygen bridges. In some embodiments, the presence of a trivalent metal ion in combination with one or more other catalytically active metal ions may cause a combined effect different than the cumulative effect of these ions when used alone. The effect primarily considered herein is on the resulting catalyst's ability to convert alcohols into hydrocarbons.

In some embodiments, only one type of trivalent metal ion aside from aluminum is incorporated into the zeolite. In other embodiments, at least two types of trivalent metal ions aside from aluminum are incorporated into the zeolite. In yet other embodiments, at least three types of trivalent metal ions aside from aluminum are incorporated into the zeolite. In yet other embodiments, precisely two or three types of trivalent metal ions aside from aluminum are incorporated into the zeolite.

Each of the trivalent metal ions can be included in any suitable amount, such as, precisely, at least, less than, or up to, for example, 0.01%, 0.02%, 0.03%, 0.04%, 0.05%, 0.06%, 0.07%, 0.08%, 0.09%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5%, or an amount within a range bounded by any two of the foregoing values. Alternatively, the total amount of trivalent metal ions (other than Al) may be limited to any of the foregoing values. In some embodiments, one or more specific types, or all, trivalent metal ions other than Al are excluded from the catalyst.

In a first set of embodiments, at least one trivalent metal ion is selected from trivalent transition metal ions. The one or more transition metals can be selected from any or a select portion of the following types of transition metals: elements of Groups IIIB (Sc group), IVB (Ti group), VB (V group), VIB (Cr group), VIIB (Mn group), VIIIB (Fe and Co groups) of the Periodic Table of the Elements. Some examples of trivalent transition metal ions include $Sc^{+3}$, $Y^{+3}$, $V^{+3}$, $Nb^{+3}$, $Cr^{+3}$, $Fe^{+3}$, and $Co^{+3}$. In other embodiments, the trivalent metal ion excludes all transition metal ions, or alternatively, excludes any one, two, or more classes or specific examples of transition metal ions provided above. In particular embodiments, the trivalent transition metal ions include $Sc^{+3}$, or $Fe^{+3}$, or a combination thereof.

In a second set of embodiments, at least one trivalent metal ion is selected from trivalent main group metal ions. The one or more main group metals can be selected from any or a select portion of elements of Group IIIA (B group) and/or Group VA (N group) of the Periodic Table, other than aluminum. Some examples of trivalent main group metal ions include $Ga^{+3}$, $In^{+3}$, $As^{+3}$, $Sb^{+3}$, and $Bi^{+3}$. In other embodiments, the trivalent metal ion excludes all main group metal ions other than aluminum, or alternatively, excludes any one, two, or more classes or specific examples of main group metal ions provided above. In particular embodiments, the trivalent main group metal ions include at least $In^{3+}$.

In a third set of embodiments, at least one trivalent metal ion is selected from trivalent lanthanide metal ions. Some examples of trivalent lanthanide metal ions considered herein include $La^{+3}$, $Ce^{+3}$, $Pr^{+3}$, $Nd^{+3}$, $Sm^{+3}$, $Eu^{+3}$, $Gd^{+3}$, $Tb^{+3}$, $Dy^{+3}$, $Ho^{+3}$, $Er^{+3}$, $Tm^{+3}$, $Yb^{+3}$, and $Lu^{+3}$. In particular embodiments, the trivalent lanthanide metal ion is selected from one or a combination of $La^{+3}$, $Ce^{+3}$, $Pr^{3+}$, and $Nd^{+3}$. In further particular embodiments, the trivalent lanthanide metal ion is or includes $La^{+3}$. In other embodiments, the trivalent metal ion excludes all lanthanide metal ions, or alternatively, excludes any one, two, or more classes or specific examples of lanthanide metal ions provided above.

In a fourth set of embodiments, the catalyst includes at least two trivalent metal ions selected from trivalent transition metal ions. Some combinations of trivalent transition metal ions considered herein include $Sc^{+3}$ in combination with one or more other trivalent transition metal ions, or $Fe^{+3}$ in combination with one or more other trivalent transition metal ions, or $Y^{+3}$ in combination with one or more other trivalent transition metal ions, or $V^{+3}$ in combination with one or more other trivalent transition metal ions.

In a fifth set of embodiments, the catalyst includes at least two trivalent metal ions selected from trivalent main group metal ions. Some combinations of trivalent main group metal ions considered herein include $In^{+3}$ in combination with one or more other trivalent main group metal ions, or $Ga^{+3}$ in combination with one or more other trivalent main group metal ions, or $As^{+3}$ in combination with one or more other trivalent main group metal ions.

In a sixth set of embodiments, the catalyst includes at least two trivalent metal ions selected from trivalent lanthanide metal ions. Some combinations of trivalent lanthanide metal ions considered herein include $La^{+3}$ in combination with one or more other trivalent lanthanide metal ions, or $Ce^{+3}$ in combination with one or more other trivalent lanthanide metal ions, or $Pr^{+3}$ in combination with one or more other trivalent lanthanide metal ions, or $Nd^{+3}$ in combination with one or more other trivalent lanthanide metal ions.

In a seventh set of embodiments, the catalyst includes at least one trivalent transition metal ion and at least one trivalent lanthanide metal ion. For example, in particular embodiments, at least one trivalent metal ion is selected from $Sc^{+3}$, $Fe^{+3}$, $V^{+3}$, and/or $Y^{+3}$, and another trivalent metal ion is selected from $La^{+3}$, $Ce^{+3}$, $Pr^{+3}$, and/or $Nd^{+3}$.

In an eighth set of embodiments, the catalyst includes at least one trivalent transition metal ion and at least one trivalent main group metal ion. For example, in particular embodiments, at least one trivalent metal ion is selected from $Sc^{+3}$, $Fe^{+3}$, $V^{+3}$, and/or $Y^{+3}$, and another trivalent metal ion is selected from $In^{+3}$, $Ga^{+3}$, and/or $In^{+3}$.

In a ninth set of embodiments, the catalyst includes at least one trivalent main group metal ion and at least one trivalent lanthanide metal ion. For example, in particular embodiments, at least one trivalent metal ion is selected from $In^{+3}$, $Ga^{+3}$, and/or $In^{+3}$, and another trivalent metal ion is selected from $La^{+3}$, $Ce^{+3}$, $Pr^{+3}$, and/or $Nd^{+3}$.

In a tenth set of embodiments, the catalyst includes at least three trivalent metal ions. The at least three trivalent metal ions can be selected from trivalent transition metal ions, trivalent main group metal ions, and/or trivalent lanthanide metal ions.

In particular embodiments, one, two, three, or more trivalent metal ions are selected from $Sc^{+3}$, $Fe^{+3}$, $V^{+3}$, $Y^{+3}$, $La^{+3}$, $Ce^{+3}$, $Pr^{+3}$, $Nd^{+3}$, $In^{+3}$, and/or $Ga^{+3}$. In more particular embodiments, one, two, three, or more trivalent metal ions are selected from $Sc^{+3}$, $Fe^{+3}$, $V^{+3}$, $La^{+3}$, and/or $In^{+3}$.

The zeolite catalyst described above is typically not coated with a metal-containing film or layer. However, the instant invention also contemplates the zeolite catalyst described above coated with a metal-containing film or layer as long as the film or layer does not substantially impede the catalyst from effectively functioning as a conversion catalyst, as intended herein. By being coated, the film or layer resides on the surface of the zeolite. In some embodiments, the surface of the zeolite refers to only the outer surface (i.e., as defined by the outer contour area of the zeolite catalyst), while in other embodiments, the surface of the zeolite refers to or includes inner surfaces of the zeolite, such as the surfaces within pores or channels of the zeolite. The metal-containing film or layer can serve, for example, to adjust the physical characteristics of the catalyst, the catalytic efficiency, or catalytic selectivity. Some examples of metal-containing surfaces include the oxides and/or sulfides of the alkali metals, alkaline earth metals, and divalent transition or main group metals, provided that such surface metals are non-contaminating to the hydrocarbon product and non-deleterious to the conversion process.

The catalyst described herein can be synthesized by any suitable method known in the art. The method considered herein should preferably incorporate the metal ions homogeneously into the zeolite. The zeolite may be a single type of zeolite, or a combination of different zeolite materials.

In particular embodiments, the catalyst described herein is prepared by, first, impregnating the zeolite with the metals to be loaded. The impregnating step can be achieved by, for example, treating the zeolite with one or more solutions containing salts of the metals to be loaded. By treating the zeolite with the metal-containing solution, the metal-containing solution is contacted with the zeolite such that the solution is absorbed into the zeolite, preferably into the entire volume of the zeolite. Typically, in preparing the metal-loaded zeolite catalyst (e.g., Cu—ZSM5 or V—ZSM-5), the acid zeolite form (i.e., H—ZSM5) or its ammonium salt (e.g., $NH_4$—ZSM-5) is used as a starting material on which an exchange with metal ions (e.g., copper ions) is performed. The particulars of such metal exchange processes are well known in the art.

In one embodiment, the impregnating step is achieved by treating the zeolite with a solution that contains all of the metals to be loaded. In another embodiment, the impregnating step is achieved by treating the zeolite with two or more solutions, wherein the different solutions contain different metals or combinations of metals. Each treatment of the zeolite with an impregnating solution corresponds to a separate impregnating step. Typically, when more than one impregnating step is employed, a drying and/or thermal treatment step is employed between the impregnating steps.

The metal-impregnating solution contains at least one or more metal ions to be loaded into the zeolite, as well as a liquid carrier for distributing the metal ions into the zeolite. The metal ions are generally in the form of metal salts. Preferably, the metal salts are completely dissolved in the liquid carrier. The metal salt contains one or more metal ions in ionic association with one or more counteranions. Any one or more of the metal ions described above can serve as the metal ion portion. The counteranion can be selected from, for example, halides ($F^-$, $Cl^-$, $Br^-$, or $I^-$), carboxylates (e.g., formate, acetate, propionate, or butyrate), sulfate, nitrate, phosphate, chlorate, bromate, iodate, hydroxide, β-diketonate (e.g., acetylacetonate), and dicarboxylates (e.g., oxalate, malonate, or succinate).

In particular embodiments, the catalyst is prepared by forming a slurry containing zeolite powder and the metals to be incorporated. The resulting slurry is dried and fired to form a powder. The powder is then combined with organic and/or inorganic binders and wet-mixed to form a paste. The resulting paste can be formed into any desired shape, e.g., by extrusion into rod, honeycomb, or pinwheel structures. The extruded structures are then dried and fired to form the final catalyst. In other embodiments, the zeolite powder, metals, and binders are all combined together to form a paste, which is then extruded and fired.

After impregnating the zeolite, the metal-loaded zeolite is typically dried and/or subjected to a thermal treatment step (e.g., a firing or calcination step). The thermal treatment step functions to permanently incorporate the impregnated metals into the zeolite, e.g., by replacing $Al^{+3}$ and/or $Si^{+4}$ and forming metal-oxide bonds within the zeolite material. In different embodiments, the thermal treatment step can be conducted at a temperature of at least 100° C., 150° C., 200° C., 250° C., 300° C., 350° C., 400° C., 450° C., 500° C., 550° C., 600° C., 650° C., 700° C., 750° C., or 800° C., or within a range therein, for a time period of, for example, 15 minutes, 30 minutes, 1 hour, 2 hours, 6 hours, 12 hours, 24 hours, 30 hours, 36 hours, or 48 hours, or within a range therein. In some particular embodiments, the thermal treatment step is conducted at a temperature of at least 500° C. for a time period of at least two hours. In some embodiments, the thermal treatment step includes a temperature ramping step from a lower temperature to a higher temperature, and/or from a higher temperature to a lower temperature. For example, the thermal treatment step can include a ramp stage from 100-700° C., or vice-versa, at a rate of 1, 2, 5, or 10° C./min.

Generally, the one or more heat treatment steps for producing the metal-loaded zeolite catalyst are conducted under normal atmospheric pressure. However, in some embodiments, an elevated pressure (e.g., above 1 atm and up to 2, 5, or 10 atm) is employed, while in other embodiments, a reduced pressure (e.g., below 1, 0.5, or 0.2 atm) is employed. Furthermore, although the heat treatment steps are generally conducted under a normal air atmosphere, in some embodiments, an elevated oxygen, reduced oxygen, or inert atmosphere is used. Some gases that can be included in the processing atmosphere include, for example, oxygen, nitrogen, helium, argon, carbon dioxide, and mixtures thereof.

For the sake of providing a more descriptive example, a Cu—ZSM-5 catalyst can be prepared as follows: 2.664 g of copper acetate hydrate (i.e., $Cu(OAc)_2 \cdot 6H_2O$) is dissolved in 600 mL de-ionized water (0.015M), followed by addition of 10.005 g of H—ZSM-5 zeolite. The slurry is kept stirring for about two hours at 50° C. Cu—ZSM-5 (blue in color) is collected by filtration after cooling, washed with de-ionized water, and calcined in air at about 500° C. (10° C./min) for four hours.

The produced Cu—ZSM-5 precursor can then be further impregnated with another metal, such as iron. For example, Cu—Fe—ZSM-5 can be produced as follows: 5 g of Cu—ZSM-5 is suspended in an aqueous solution of 25 mL of 0.015M Fe(NO$_3$)$_3$, degassed with N2, and is kept stirring for about two hours at about 80° C. Brown solid is obtained after filtration, leaving a clear and colorless filtrate. The product is then calcined in air at about 500° C. (2° C./min) for about two hours. The resulting Cu—Fe—ZSM-5 catalyst typically contains about 2.4% Cu and 0.3% Fe. Numerous other metals can be loaded into the zeolite by similar means to produce a variety of different metal-loaded catalysts.

Generally, the zeolite catalyst described herein is in the form of a powder. In a first set of embodiments, at least a portion, or all, of the particles of the powder have a size less than a micron (i.e., nanosized particles). The nanosized particles can have a particle size of precisely, at least, up to, or less than, for example, 1, 2, 5, 10, 20, 30, 40, 50, 60, 70, 80, 90, 100, 150, 200, 250, 300, 350, 400, 450, 500, 550, 600, 650, 700, 750, 800, 850, 900, or 950 nanometers (nm), or a particle size within a range bounded by any two of the foregoing values. In a second set of embodiments, at least a portion, or all, of the particles of the powder have a size at or above 1 micron in size. The micron-sized particles can have a particle size of precisely, at least, up to, or less than, for example, 1, 2, 5, 10, 20, 30, 40, 50, 60, 70, 80, 90, or 100 microns (m), or a particle size within a range bounded by any two of the foregoing values. In some embodiments, single crystals or grains of the catalyst correspond to any of the sizes provided above, while in other embodiments, crystals or grains of the catalyst are agglomerated to provide agglomerated crystallites or grains having any of the above exemplary dimensions.

In other embodiments, the zeolite catalyst can be in the form of a film, a coating, or a multiplicity of films or coatings. The thickness of the coatings or multiplicity of coatings can be, for example, 1, 2, 5, 10, 50, or 100 microns, or a range therein, or up to 100 micron thickness. In yet other embodiments, the zeolite catalyst is in the form of a non-particulate (i.e., continuous) bulk solid. In still other embodiments, the zeolite catalyst can be fibrous or in the form of a mesh.

The catalyst can also be mixed with or affixed onto a support material suitable for operation in a catalytic converter. The support material can be a powder (e.g., having any of the above particle sizes), granular (e.g., 0.5 mm or greater particle size), a bulk material, such as a honeycomb monolith of the flow-through type, a plate or multi-plate structure, or corrugated metal sheets. If a honeycomb structure is used, the honeycomb structure can contain any suitable density of cells. For example, the honeycomb structure can have 100, 200, 300, 400, 500, 600, 700, 800, or 900 cells per square inch (cells/in$^2$) (or from 62-140 cells/cm$^2$) or greater. The support material is generally constructed of a refractory composition, such as those containing cordierite, mullite, alumina (e.g., α-, β-, or γ-alumina), or zirconia, or a combination thereof. Honeycomb structures, in particular, are described in detail in, for example, U.S. Pat. Nos. 5,314,665, 7,442,425, and 7,438,868, the contents of which are incorporated herein by reference in their entirety. When corrugated or other types of metal sheets are used, these can be layered on top of each other with catalyst material supported on the sheets such that passages remain that allow the flow of alcohol-containing fluid. The layered sheets can also be formed into a structure, such as a cylinder, by winding the sheets.

In particular embodiments, the zeolite catalyst is or includes a pentasil-type composition loaded with any of the suitable metals described above. In more specific embodiments, the zeolite catalyst is, or includes, for example, copper-loaded ZSM5 (i.e., Cu—ZSM5), Fe—ZSM5, Cu,Fe—ZSM5, or a mixture of Cu—ZSM5 and Fe—ZSM5. In other embodiments, the zeolite catalyst is, or includes, for example, Cu—La—ZSM5, Fe—La—ZSM5, Fe—Cu-La—ZSM5, Cu—Sc—ZSM5, or Cu—In—ZSM5.

Examples have been set forth below for the purpose of illustration and to describe certain specific embodiments of the invention. However, the scope of this invention is not to be in any way limited by the examples set forth herein.

Example 1

Preparation of Cu—ZSM5 Catalyst

NH$_4$—ZSM-5 was purchased from Zeolyst International (CBV-2314) with a SiO$_2$/Al$_2$O$_3$ ratio of 23 and used as received. The calcination of NH$_4$—ZSM-5 at 500° C. for four hours furnished H—ZSM-5 in quantitative yield. A 2.664 g sample of commercially available Cu(OOCCH$_3$)$_2$·H$_2$O was dissolved in 600 mL de-ionized water to make a 22 mole solution. A 10.0 g sample of H—ZSM-5 was added to the copper acetate solution and the suspension stirred at 50° C. for two hours. A blue-colored solid was collected by filtration after cooling and washed with de-ionized water, dried, and calcined in air at 500° C. for four hours to obtain Cu—ZSM-5. Elemental analysis shows 2.76% Cu and 3.31% Al in the sample.

Example 2

Preparation of Fe—ZSM-5 Catalyst

A 12 g sample of H—ZSM-5 was suspended in degassed 0.02 M Fe(NO$_3$)$_3$ aqueous solution. The suspension was stirred at room temperature for 24 hours. A light pink-colored solid was collected by filtration and washed with de-ionized water, dried, and calcined in air at 550° C. for four hours to obtain 9.98 g of Fe—ZSM-5. Elemental analysis shows 776 ppm of iron.

Example 3

Preparation of CuFe—ZSM-5 Catalyst

A 5 g sample of Cu—ZSM-5 was suspended in a 25 mL aqueous solution of 0.015 M Fe(NO$_3$)$_3$, degassed with N2, and was kept stirring for two hours at 80° C. A brown solid was collected from the reaction mixture by filtration while rejecting a clear and colorless filtrate. The powder was calcined in air at 500° C. (2° C./min) for two hours to obtain a pale yellow powder of CuFe—ZSM-5. Elemental analyses: Cu 2.39%; Fe 0.40%; Al 2.97%.

Example 4

Preparation of V—ZSM-5 Catalyst

NH$_4^+$—ZSM-5 (SiO$_2$/Al$_2$O$_3$=23) starting material, as commercially obtained, was ion-exchanged with V(III)Cl$_3$ in aqueous solution. Specifically, a 0.050 M solution of V(III)Cl$_3$ was first made by dissolving 2.5 g of V(III)Cl$_3$ into 320 mL of distilled water. Then, 12.17 g of NH$_4^+$—ZSM-5 was added to the aqueous solution and warmed to 80° C. After stirring for eight hours, the heterogeneous mixture was vacuum filtered, and the filtrate discarded. The light blue V—ZSM-5 initial solid product was then calcined at 500° C. for four hours, which resulted in a light yellow final solid product.

Example 5

Alcohol-to-Hydrocarbon Conversion Performance Using Cu—ZSM-5 Catalyst

A catalytic reactor was loaded with 1.0 g of Cu—ZSM-5 powder and heated to 500° C. for four hours under a flow of dry helium. The catalyst was cooled to 400° C. and 10% aqueous ethanol was introduced into the reactor employing a syringe pump at a rate of 6.8 mL/hour. This corresponds to a liquid hourly space velocity (LHSV) of 2.5 $h^{-1}$. The post-catalyst emissions were collected in a U-tube immersed in liquid nitrogen. On warming the contents of the U-tube, an aqueous emulsion was obtained. A sample of this emulsion was injected into a Gas Chromatograph Mass Spectrometer (GCMS). The trace obtained from GCMS is shown in FIG. 1(B). This is compared in FIG. 1(A) with the trace of emulsion obtained when pure ethanol was injected into the reactor loaded with Cu—ZSM-5. A comparison of GCMS trace of pure and 10% aqueous ethanol shows that aqueous dilution has no effect on conversion or product distribution when the reaction is conducted under the conditions described above.

Figure 2:
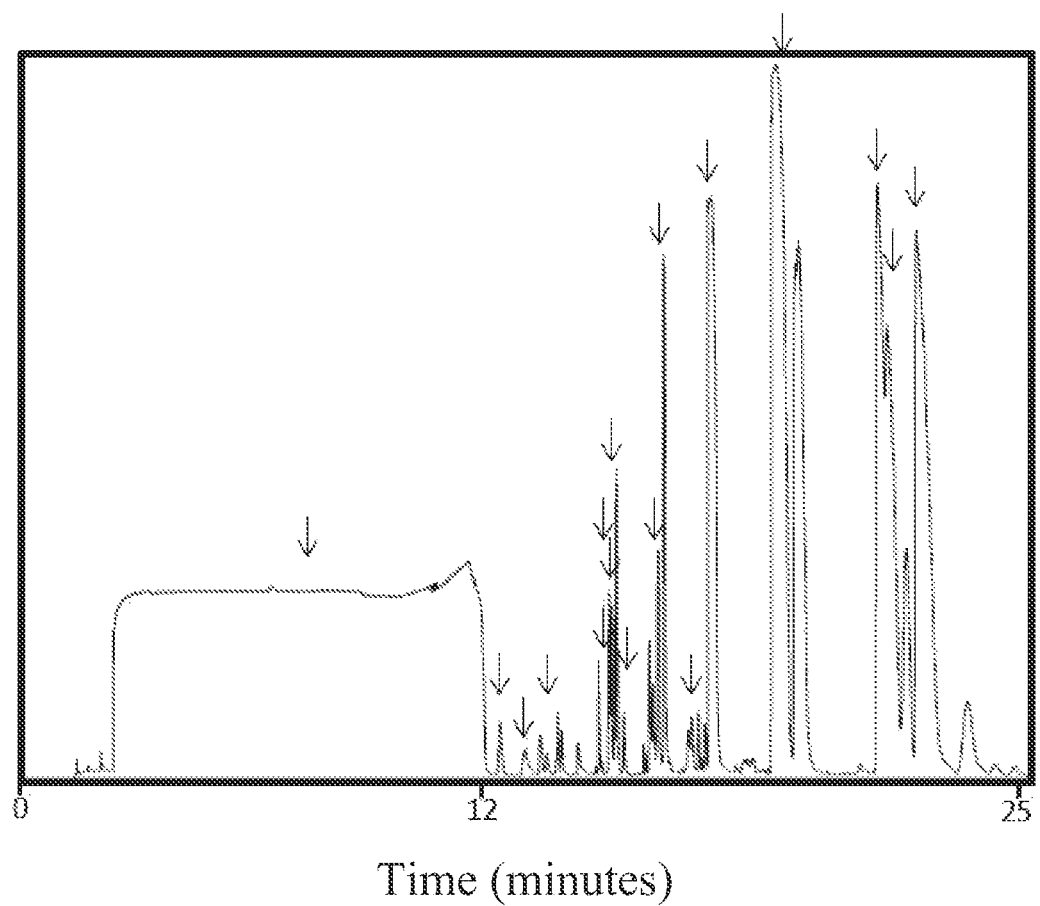
FIG. 2. Graph showing hydrocarbon distribution in product stream of 10% ethanol after catalytic conversion over Cu—ZSM-5 at 400° C. at 12.5 h$^{-1}$ LHSV. The compounds are (from left to right, identified by arrows) water, acetaldehyde, isobutane, 2-butene, acetone, 2-methylbutene, 2-methyl-2-butene, cis-1,2-dimethylcyclopropene, cyclopentane, 3,3-dimethylcyclobutene, benzene, 4,4-dimethylcyclobutane, toluene, 1,3-dimethylbenzene, 1-ethyl-3-methylbenzene, 1,2,4-trimethylbenzene, and 1-ethyl-4-methylbenzene.

The experiment was also conducted with a LHSV of 12.5 $h^{-1}$ for aqueous ethanol. As shown by FIG. 2, identical results were obtained in terms of quantitative conversion and product distribution. The broad peak between 2.5 and 12.5 minutes is due to water. The peaks that appear after 12.5 minutes were identified to be due to acetaldehyde, isobutane, 2-butene, acetone, 2-methylbutene, 2-methyl-2-butene, cis-1,2-dimethylcyclopropene, cyclopentane, 3,3-dimethylcyclobutene, benzene, 4,4-dimethylcyclobutane, toluene, 1,3-dimethylbenzene, 1-ethyl-3-methylbenzene, 1,2,4-trimethylbenzene, and 1-ethyl-4-methyl-benzene.

Example 6

Alcohol-to-Hydrocarbon Conversion Performance Using V—ZSM-5 Catalyst

Figures 3A, 3B:
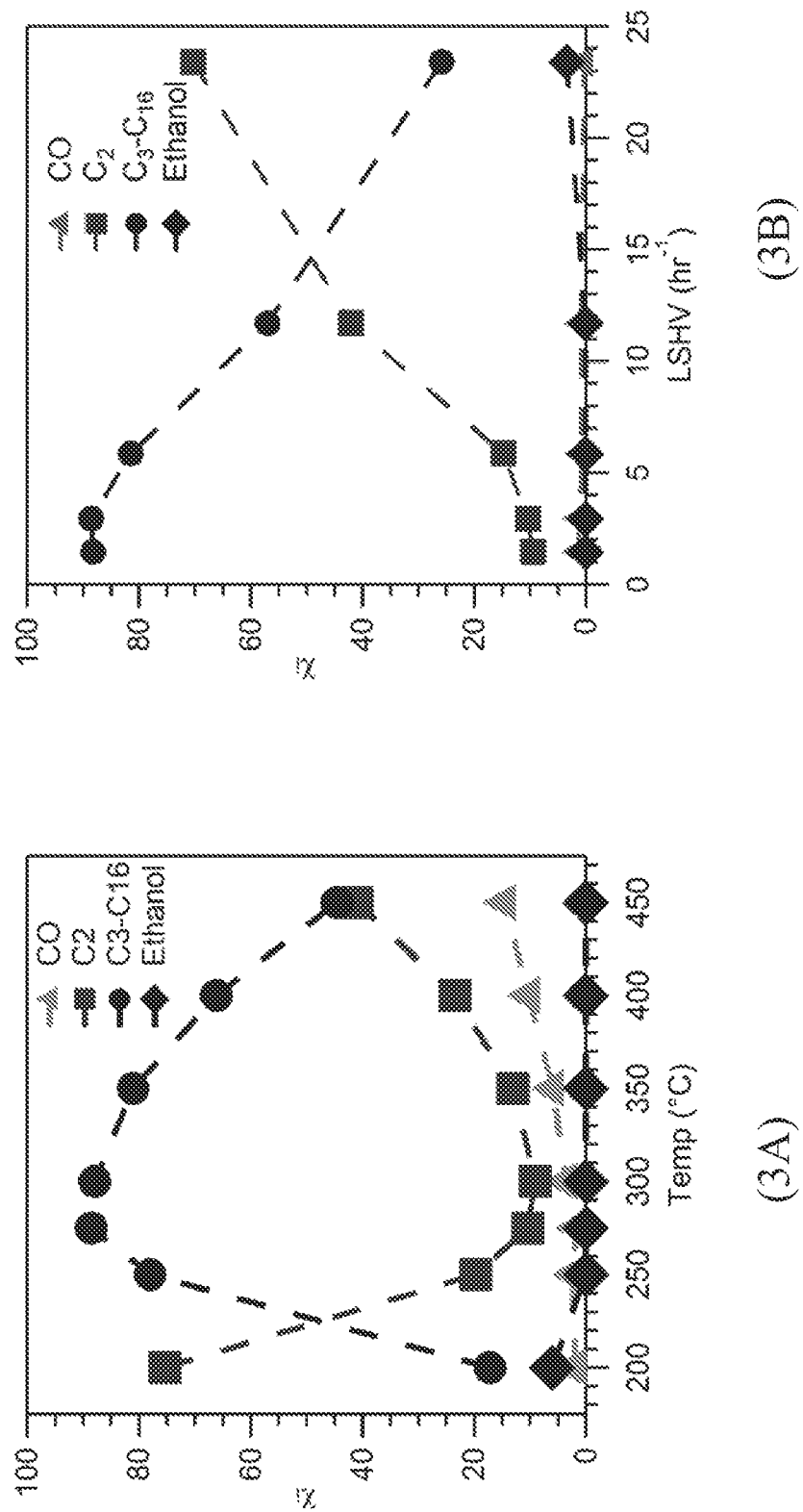
FIGS. 3A, 3B. Graph plotting ethanol conversion to hydrocarbons as a function of temperature at a LHSV of 2.93 h$^{-1}$ (FIG. 3A) and as a function of LHSV at 275° C.

A catalytic reactor was loaded with 1.0 g of V—ZSM-5 powder and heated to 500° C. for four hours under a flow of dry helium. The catalyst was cooled to 200° C., and pure ethanol was introduced into the reactor employing a syringe pump at 5.0 mL/hour. This corresponds to a LHSV of 2.93 $h^{-1}$. The post-catalyst emissions were analyzed by on-line gas chromatography by gradually increasing the temperature to 450° C. The data is shown in FIGS. 3A and 3B. The results show that a reaction temperature of 275° C. is ideal in this instance for minimizing ethylene (designated as "C2") by-product with negligible CO, which suggests a minimal level of product decomposition on the catalyst surface. The conversion of ethanol at 275° C. as a function of space velocity was also monitored, and a LHSV of 2.93 $h^{-1}$ was determined to be optimal for the same reasons.

Figure 4A:
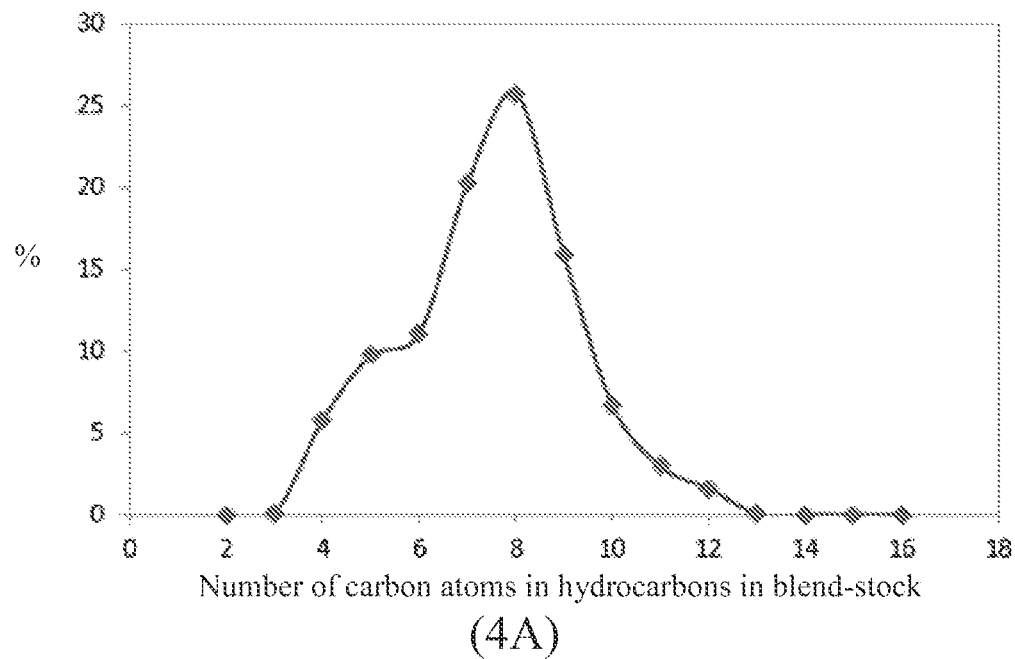
FIGS. 4A, 4B. Graph plotting carbon distribution in produced blend-stock (FIG. 4A) and diesel/jet fuel blend-stock obtained by fractional collection (FIG. 4B) for V—ZSM-5 catalyst.
Figure 4B:
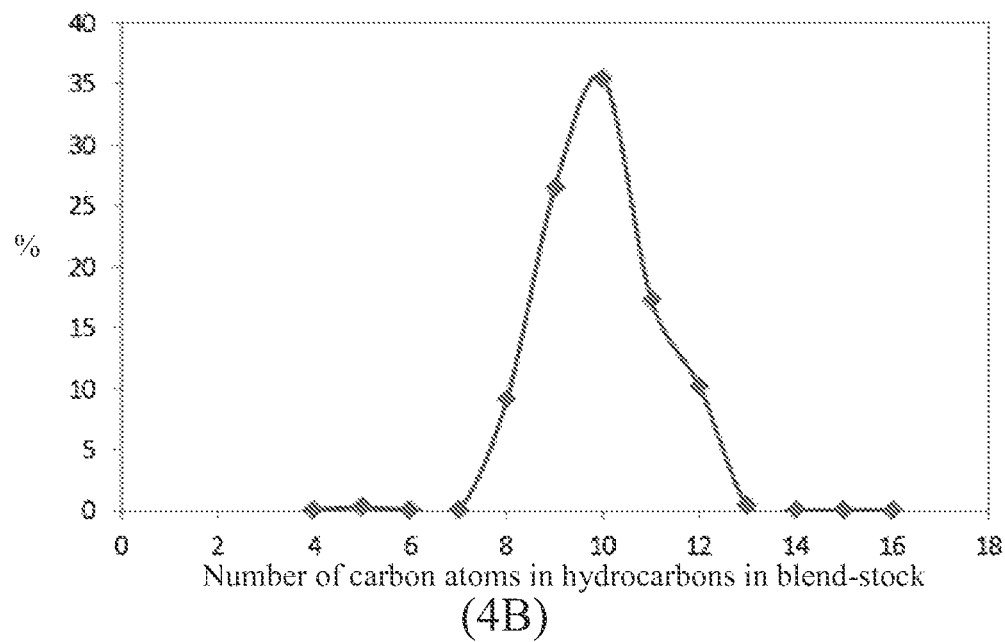

The catalytic emissions were collected in a cold trap immersed in liquid nitrogen. On warming, the hydrocarbon layer and aqueous layer were separated. As can be elucidated from the carbon distribution plot shown in FIG. 4A, the hydrocarbon produced from ethanol (designated as "C3-C16") was found to be a mixture of about 2.47% paraffins, 10.5% iso-paraffins, 9.65% olefins, 3.11% naphthalenes, and 74.26% aromatics. The average molecular weight of the hydrocarbon mixture was found to be 97.86, the average specific gravity 0.823, total hydrogen 10.5, and the carbon to hydrogen ratio 8.47. The calculated research and motor octane numbers were found to be 107.6 and 93.3, respectively. Fractional collection permitted collection of 160-300° C. blend-stocks suitable for mixing with diesel or jet fuel. The carbon distribution is shown in FIG. 4B. The average molecular weight of the hydrocarbon mixture was found to be 129.97, the average specific gravity total hydrogen 9.4, and the carbon to hydrogen ratio 9.63.

Engine tests were conducted on a modified Sturman variable valve actuation engine with a ported fuel injection that can be warmed up using a gasoline direct injection fueling system without consuming test fuel. Test fuel or certification gasoline was then introduced, and performance data recorded, such as cylinder pressure and heat release rate as a function of crank angle. The parameters used for engine operation on the instant blend stock were found to be identical to parameters for engine operation using certification gasoline.

While there have been shown and described what are at present considered the preferred embodiments of the invention, those skilled in the art may make various changes and modifications which remain within the scope of the invention defined by the appended claims.

What is claimed is:

1. A system for converting ethanol to a mixture of hydrocarbon compounds useful as a fuel or as a blendstock component of a fuel, comprising:
   a source of a feedstock comprising ethanol, wherein the ethanol is in an aqueous solution at a concentration of no more than about 20% (vol/vol);
   a boiler unit in fluidic communication with the source of the feedstock and configured to volatilize the feedstock; and
   a reactor unit in fluidic communication with the boiler unit and configured to house a catalyst catalytically active for directly converting the ethanol to a mixture of hydrocarbons, wherein the catalyst consists of a zeolite loaded with at least one positively-charged metal ion selected from the group consisting of alkali metal ion, alkaline earth metal ion, lanthanide metal ion, copper ion, zinc ion, titanium ion, vanadium ion, cadmium ion, gallium ion, and indium ion, and wherein said mixture of hydrocarbon compounds substantially corresponds to a fuel selected from gasoline, kerosene, diesel, and jet propellant.

2. The system of claim 1, wherein the ethanol is produced by a fermentation process.

3. The system of claim 1, wherein the system is integrated with a fermentation process that generates the feedstock.

4. The system of claim 3, wherein the fermentation process is fluidically connected to the system.

5. The system of claim 3, wherein the fermentation process comprises biomass.

6. The system of claim 5, wherein said biomass comprises lignocellulosic matter.

7. The system of claim 3, wherein the fermentation process produces the alcohol from a plant-based source of sugars.

8. The system of claim 1, wherein the at least one positively charged metal ion is selected from alkali metal, alkaline earth metal, copper, vanadium, zinc, titanium, cadmium, gallium, indium, and combinations thereof.

9. The system of claim 1, wherein the at least one positively charged metal ion is selected from copper, and vanadium.

10. The system of claim 1, wherein the zeolite comprises a pentasil zeolite.

11. The system of claim 10, wherein the pentasil zeolite comprises ZSM5.

12. The system of claim 1, wherein the reactor unit is a single reactor unit.

13. The system of claim 1, wherein said catalyst consists of a single metal-loaded zeolite catalyst.

* * * * *